United States Patent [19]

Power et al.

[11] Patent Number: 5,703,072
[45] Date of Patent: *Dec. 30, 1997

[54] BICYCLIC NONANE AND DECANE COMPOUNDS HAVING DOPAMINE RECEPTOR AFFINITY

[75] Inventors: Patricia L. Power, Guelph; Sumanas Rakhit, Mississauga, both of Canada

[73] Assignee: Allelix Biopharmaceuticals, Ontario, Canada

[*] Notice: The term of this patent shall not extend beyond the expiration date of Pat. No. 5,576,314.

[21] Appl. No.: 625,358

[22] Filed: Apr. 1, 1996

Related U.S. Application Data

[63] Continuation-in-part of Ser. No. 354,906, Dec. 12, 1994, Pat. No. 5,576,314.
[51] Int. Cl.$^6$ .................. A61K 31/55; C07D 471/04; C07D 487/04
[52] U.S. Cl. ........................... 514/211; 540/551
[58] Field of Search ................ 540/551; 514/211

[56] References Cited

U.S. PATENT DOCUMENTS 5,576,314  11/1996  Power et al. ................ 514/211

*Primary Examiner*—Philip I. Datlow
*Attorney, Agent, or Firm*—Nikaido, Marmelstein, Murray & Oram LLP

[57] ABSTRACT

Described herein are D4 receptor-selective compounds of the general formula:

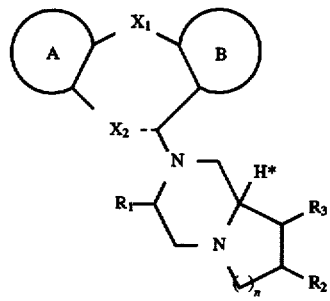

wherein:
A and B are independently selected, substituted or unsubstituted, unsaturated 5- or 6-membered, homo- or heterocyclic rings;
$X_1$ is selected from O, S, SO, $SO_2$, $CH_2$, C=O, CH—OH, CH—N($C_{1-4}$alkyl)$_2$, C=CHCl, and C=CHCN;
$X_2$— is selected from N=, $CH_2$—, CH= and C(O)—;
n is 1 or 2;
$R_1$ is selected from H and the α-carbon side chain of an amino acid;
$R_2$ and $R_3$ are selected independently from H, OH, —$NH_2$, —C(O)$NH_2$=O, =S, halo, cyano, $C_{1-9}$alkyl, $C_{1-9}$alkoxy, $C_{1-4}$alkylS—, $C_{1-4}$alkylSO—, $C_{1-4}$alkylSO$_2$—, phenoxy, benzyloxy and piperonyloxy; and
H* is in either the R- or the S-configuration,
and acid addition salts, solvates and hydrates thereof.

Their use as ligands for dopamine receptor identification and in a drug screening program, and as pharmaceuticals to treat indications in which the D4 receptor is implicated, such as schizophrenia, is also described.

43 Claims, No Drawings

BICYCLIC NONANE AND DECANE COMPOUNDS HAVING DOPAMINE RECEPTOR AFFINITY

CROSS REFERENCE TO RELATED APPLICATION

This application is a continuation-in-part of U.S. Ser. No. 08/354,906 filed Dec. 12, 1994, now U.S. Pat. No. 5,576,314.

This invention relates to compounds that bind to the dopamine D4 receptor, to their preparation and their use for therapeutic and drug screening purposes.

BACKGROUND TO THE INVENTION

Neuronal cell receptors that bind the neurotransmitter dopamine constitute a group of at least five structurally distinct proteins that can now be produced using recombinant DNA techniques. These techniques have been applied to construct cell lines that incorporate the dopamine receptor in their membranes, to provide regenerable and homogeneous substrates with which chemical libraries can be screened to identify potential CNS-active drugs.

Recent evidence strongly implicates the dopamine receptor classified as D4 in the etiology of schizophrenia. It has been suggested that compounds capable of interfering with the function of this receptor, which is present in schizophrenics at levels that are six times normal, would be useful in the treatment of this disease (Seeman et al, Nature, 1993, 365:441). Some drugs currently on the market in fact exhibit the desired antagonism of D4 receptor activity, and bind with relative strong affinity to the receptor. Yet because of their structure, these drugs interact also with related dopamine receptors, particularly the D2 receptor type, which results in significant side effects that include altered motor function and tachycardia. It would be desirable to provide compounds that exhibit not only a high degree of affinity for the D4 receptor, but also a relatively low degree of affinity for the D2 receptor. In this specification, this desired combination of receptor binding properties is referred to as D4 selectivity.

Products currently marketed to treat indications in which the D4 receptor function is implicated include the dibenzodiazepine, clozapine, and the dibenzoxazepine, isoloxapine. Analysis of their dopamine receptor binding properties has shown that the preference for binding the D4 receptor relative to the D2 receptor is about 10 fold, for both products. Similarly, both bind the D4 receptor with about the same affinity (Ki value approximately 20 nM). Other products, recently published in the scientific literature, have shown similar D4 to D2 selectivity profile and D4 affinity values.

It is an object of the present to provide a compound that binds to the D4 receptor.

It is an object of the present invention to provide a compound having an improved D4 selectivity profile.

It is another object of the present invention to provide a compound having an improved D4 binding affinity.

It is another object of the present invention to provide a compound having both an improved D4 selectivity profile and D4 binding affinity.

It is a further object of the present invention to provide a pharmaceutical composition comprising a compound of the present invention, as active ingredient.

SUMMARY OF THE INVENTION

According to one aspect of the present invention, there is provided a compound of Formula I:

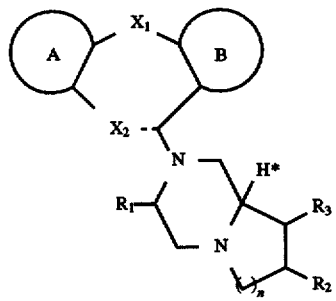

wherein:

A and B are independently selected, substituted or unsubstituted, unsaturated 5- or 6-membered, homo- or heterocyclic rings;

$X_1$ is selected from O, S, SO, $SO_2$, $CH_2$, C=O, CH—OH, CH—N($C_{1-4}$alkyl)$_2$, C=CHCl, and C=CHCN;

$X_2$— is selected from N=, $CH_2$—, CH= and C(O)—;

n is 1 or 2;

$R_1$ is selected from H and the α-carbon side chain of an amino acid;

$R_2$ and $R_3$ are selected independently from H, OH, —$NH_2$, —C(O)$NH_2$, =O, =S, halo, cyano, $C_{1-9}$alkyl, $C_{1-9}$alkoxy, $C_{1-4}$alkylS—, $C_{1-4}$alkylS O—, $C_{1-4}$alkylSO$_2$—, phenoxy, benzyloxy and piperonyl;

and H* is in either the R- or the S-configuration, and acid addition salts, solvates and hydrates thereof.

According to another aspect of the invention, there is provided a pharmaceutical composition comprising a compound of Formula I and a pharmaceutically acceptable carrier.

In another of its aspects the invention provides the use of compounds of the present invention, as D4 receptor antagonists for the treatment of medical conditions mediated by D4 receptor stimulation.

In a further aspect of the invention, there is provided an analytical method in which a compound of the invention is used to distinguish, in a receptor population, the D4 receptor from other receptor types, and particularly from the D2 receptor. These and other aspects of the present invention are now described in greater detail hereinbelow.

DETAILED DESCRIPTION AND PREFERRED EMBODIMENTS

The invention relates to compounds that bind the dopamine D4 receptor in a selective manner, relative to the dopamine D2 receptor. It has been found, more particularly, that the D4 selectivity of D4-binding ligands having the tricyclic structure:

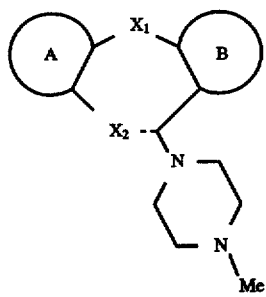

is significantly improved when the piperazine group is derivatized to form the bicyclic moiety of the structure:

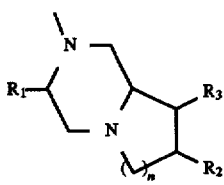

In accordance with one of its aspects, the present invention accordingly provides compounds that conform to Formula I:

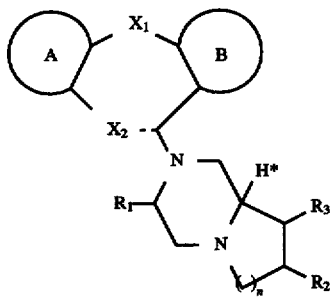

In the bicyclic moiety, $R_1$ is selected from H and an amino acid side chain. It is to be understood that the term "amino acid side chain" refers to the α-carbon side chain on amino acids, and particularly the side chain of naturally occurring amino acids in either D or L orientation and derivatives thereof. Particular embodiments of the invention include those in which $R_1$ is selected from H, OH, $C_{1-4}$alkyl such as methyl, isopropyl, isobutyl, HS—$C_{1-4}$alkylene, $H_2N$—$C_{1-4}$alkylene, HOOC—$C_{1-4}$alkylene, guanidino-$C_{1-4}$alkylene and $H_2NC(O)$—$C_{1-4}$alkylene. In a specific embodiment of the invention, $R_1$ is H.

In embodiments of the invention, $R_2$ and $R_3$ are selected desirably from H, halo, OH, $C_{1-9}$alkyl, $C_{1-9}$alkoxy, and benzyloxy. Specific embodiments of the invention include those in which $R_2$ is H, OH or benzyloxy and R3 is H.

In specific embodiments of the invention, the bicyclic moiety coupled to the tricyclic structure may be a 1,4-diazabicyclo[4.3.0]nonane (when n=1) or a 1,4-diazabicyclo[4.4.0]decane (when n=2).

In a specific embodiment of the invention, the chiral carbon at the 6-position of the nonane bicycle or decane bicycle (represented by H*) is oriented in the S configuration, and preparations containing such compounds are essentially free of the corresponding 6R-enantiomer.

According to specific embodiments of the invention, the bicyclic moiety is one selected from the following:

(S)-1,4-diazabicyclo[4.3.0]nonane;
(R)-1,4-diazabicyclo[4.3.0]nonane;
(S)-1,4-diazabicyclo[4.4.0]decane;
(R)-1,4-diazabicyclo[4.4.0]decane;
(R,S)-1,4-diazabicyclo[4.4.0]decane;
(6S,8S)-8-benzyloxy-1,4-diazabicyclo[4.3.0]nonane;
(6S,8S)-8-t-butoxy-1,4-diazabicyclo[4.3.0]nonane; and
(3S,6S)-3-methyl-1,4-diazabicyclo[4.3.0]nonane.

The tricyclic moiety to which the bicyclic moiety is coupled can have various structures and will typically incorporate those found to be important for dopamine D4 receptor binding. In other words, the tricycles suitable for coupling to the bicycle are those which, when substituted by functions other than the bicyclic moiety, are determined by the assay herein described, to bind the D4 receptor (preferably the human D4 receptor) with an affinity of at least 1 μM (Ki). In particular, the rings A and B are selected, according to embodiments of the invention, from benzene, pyridine, pyrimidine, pyrazine, pyridazine, pyrole, imidazole, triazole, pyrazole, thiophene, thiazole, furan, and pyran. In a particular embodiment, ring A is selected from benzene and pyridine and ring B is selected from benzene, pyridine, pyrimidine, pyrazine, pyridazine, pyrole, imidazole, triazole, pyrazole, thiophene, thiazole, furan and pyran; and is particularly selected from benzene and pyridine. In specific embodiments of the invention, both rings A and B are optionally substituted benzene. It is to be appreciated that when rings A and B are heterocycles, the heteroatoms are shared with the central seven membered ring only when the shared heteroatom is N. Such tricycles are within the scope of the Formula I; one embodiment of which is described by Lednicer et al in The Organic Chemistry of Drug Synthesis, (1992, John Wiley & Sons Inc., New York) wherein ring B is imidazole that is fused to a thiazepine at one of the imidazole nitrogen atoms.

One or both rings A and B may be substituted with from 1 to 3, usually 1 or 2, substituents. When substituted, the substituents are selected from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, halo-substituted $C_{1-4}$acyl, cyclo-$C_{3-7}$alkyl, thio-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$ alkylsulfonyl, halosulfonyl, halo-substituted $C_{1-4}$alkylsulfonyl, $C_{1-4}$alkylsulfoxyl, sulfonamido, $C_{1-4}$alkylseleno, and $OSO_3H$, Substitution sites on rings A and B will be limited in practice to the carbon atoms on the ring that are not shared with the central seven membered ring. For example, a benzene ring can accomodate up to 4 substituents; pyridine, and pyran rings can accomodate up to 3 substituents; pyrimidine, pyrazine, pyridazine, pyrole, furan and thiophene rings can accomodate up to 2 substituents; imidazole, pyrazole and thiazole rings can accomodate only 1 substituent; and a triazole ring can accomodate no substituents. It is also to be understood that rings A and B may incorporate substituents at nitrogen atoms on the ring that are not shared with the central seven membered ring. For example the NH member of an imidazole ring may be substituted. In particular embodiments, rings A and B are substituted with from 1 to 2 substituents selected from chloro, fluoro, methyl, trifluoromethyl, methoxy, nitro, cyano and methylthio. In particularly preferred embodiments ring A is benzene substituted with 1 or 2 substituents selected from chloro, bromo, methyl, nitro and cyano and ring B is benzene substituted with 1 or 2 substituents selected from chloro, bromo, methoxy, trifluoromethyl and nitro.

In the central, 7-membered ring of the tricycle, $X_1$ may be any one of O, S, SO, $SO_2$, C=O, $CH_2$, CH—OH, CH—N $(C_{1-4}$alkyl$)_2$, C=CHCl and C=CHCN, while $X_2$— may independently be any one of N=, $CH_2$—, CH= and C(O) —. In particular embodiments, $X_1$ is O or S and $X_2$—, independently, is N= or CH=, to form a seven-membered ring selected from oxazepine, thiazepine and thiepine. In particularly preferred embodiments, $X_1$ is O or S and $X_2$— is N=. In specific embodiments $X_1$ is O and $X_2$- is N=, to form an oxazepine.

In preferred embodiments $X_1$ and $X_2$— together with rings A and B are selected to form a tricyclic moiety that is selected from a dibenz[b,f]-1,4-oxazepine that is optionally substituted, for example with one of 8-chloro, 4-nitro, 4-amino, 4-cyano, 4-bromo, or 4-chloro; a dibenzo[b,f] thiepine that is optionally substituted, for example with one of 2-nitro or 2-chloro; an 11H-dibenzo[b,f]thiepine that is optionally substituted, for example with 2-methylthio; and a dibenzo[b,f]-1,4-thiazepine that is optionally substituted, for example with 8-chloro. In a specific embodiment of the invention, $X_1$ and $X_2$— together with rings A and B are form a tricyclic moiety, for attachment to the bicyclic moiety, which is selected from:

dibenz[b,f][1,4]oxazepine;
8-chloro-dibenz[b,f][1,4]oxazepine;
8-methyl-dibenz[b,f][1,4]oxazepine;
4-chloro-dibenz[b,f]-1,4-oxazepine;
4-bromo-dibenz[b,f]-1,4-oxazepine;
4-amino-dibenz[b,f]-1,4-oxazepine;
4-cyano-dibenz[b,f]-1,4-oxazepine;
4-nitro-dibenz[b,f]-1,4-oxazepine;
dibenzo[b,f][1,4]thiazepine;
8-chloro-dibenzo[b,f][1,4]thiazepine;
dibenzo[b,f]thiepine; and
2-nitrodibenzo[b,f]thiepine.

In specific embodiments of the invention, compounds of Formula I include:

8-chloro-11-[(R,S)-1,4-diazabicyclo[4.4.0]decan-4-yl] dibenzo[b,f]-1,4-oxazepine;
8-chloro-11-[(S)-1,4-diazabicyclo[4.3.0]non-4-yl]-dibenzo [b,f]-1,4-oxazepine;
8-chloro-11-[(R)-1,4-diazabicyclo[4.3.0]non-4-yl]-dibenzo [b,f]-1,4-oxazepine;
8-chloro-11-[(S)-1,4-diazabicyclo[4.4.0]decan-4-yl]-dibenzo[b,f]-1,4-oxazepine;
8-chloro-11-[(R)-1,4-diazabicyclo[4.4.0]decan-4-yl]-dibenzo[b,f]-1,4-oxazepine;
8-chloro-11-[(6S,8S)-8-benzyloxy-1,4-diazabicyclo[4.3.0] non-4-yl]-dibenzo[b,f]-1,4 oxazepine; and
8-chloro-11-[(6S,8S)-8-hydroxy-1,4-diazabicyclo[4.3.0] non-4-yl]-dibenzo[b,f]-1,4-oxazepine.

In a more preferred embodiment, there are provided compounds of Formula (I) exhibiting enhanced D4 selectivity, including:

8-chloro-11-[(S)-1,4-diazabicyclo[4.3.0]non-4-yl]-dibenzo [b,f]-1,4-oxazepine;
8-chloro-11-[(R)-1,4-diazabicyclo[4.3.0]non-4-yl]-dibenzo [b,f]-1,4-oxazepine;
8-chloro-11-[(S)-1,4-diazabicyclo[4.4.0]decan-4-yl]-dibenzo[b,f]-1,4-oxazepine;
8-chloro-11-[(6S,8S)-8-benzyloxy-1,4-diazabicyclo[4.3.0] non-4-yl]-dibenzo[b,f]-1,4-oxazepine; and
8-chloro-11-[(6S,8S)-8-hydroxy-1,4-diazabicyclo[4.3.0] non-4-yl]-dibenzo[b,f]-1,4-oxazepine.

In a more preferred embodiment, there are provided compounds of Formula I exhibiting enhanced D4 affinity, including:

8-chloro-11-[(R,S)-1,4-diazabicyclo[4.4.0]decan-4-yl] dibenzo[b,f]-1,4-oxazepine;
8-chloro-11-[(S)-1,4-diazabicyclo[4.3.0]non-4-yl]-dibenzo [b,f]-1,4-oxazepine;
8-chloro-11-[(R)-1,4-diazabicyclo[4.3.0]non-4-yl]-dibenzo [b,f]-1,4-oxazepine; and
8-chloro-11-[(S)-1,4-diazabicyclo[4.4.0]decan-4-yl]-dibenzo[b,f]-1,4-oxazepine;

In a most preferred embodiment, there are provided compounds of Formula I exhibiting enhanced D4 affinity and selectivity than clozapine, including:

8-chloro-11-[(S)-1,4-diazabicyclo[4.3.0]non-4-yl]-dibenzo [b,f]-1,4-oxazepine;
8-chloro-11-[(R)-1,4-diazabicyclo[4.3.0]non-4-yl]-dibenzo [b,f]-1,4-oxazepine; and
8-chloro-11-[(S)-1,4-diazabicyclo[4.4.0]decan-4-yl]-dibenzo[b,f]-1,4-oxazepine;

Acid addition salts of the compound of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

It will be appreciated that certain compounds of Formula I may contain an asymmetric centre. Such compounds will exist as two (or more) optical isomers (enantiomers). Both the pure enantiomers and the racemic mixtures (50% of each enantiomer), as well as unequal mixtures of the two, are included within the scope of the present invention. Further, all diastereomeric forms possible (pure enantiomers and mixtures thereof) are within the scope of the invention. As noted hereinabove, H* at position 6 of the bicyclic moiety is most desirably in the S-configuration, and the compounds of the invention are preferably in a form essentially free from R-enantiomer.

The compounds of the present invention can be prepared by processes analogous to those known in the art. The present invention therefore provides, in a further aspect, a process for the preparation of a compound of Formula I or a salt, solvate or hydrate thereof, which comprises the step of coupling a reagent of Formula A:

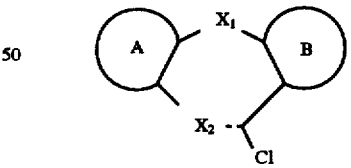

with a reagent of Formula B:

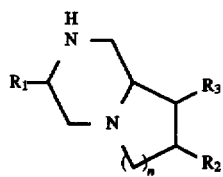

in the presence of diisopropylethylamine in acetonitrile (DIEA).

The chloro reagent (A), can be obtained commercially or can be synthesized using established techniques, for example, by treating the corresponding ketone (reagent Q) with $PCl_5$. Reagent Q may itself be commercially available or synthesized. For example, when $X_1$ is O and $X_2$— is N= (an oxazepine), reagent (Q) may be prepared according to the procedures described by Klunder (J. Med. Chem. 1992, 35:1887) by condensation of a 2-aminophenol with 2-chloro-5-nitrobenzoyl chloride in THF to afford the corresponding carboxamide followed by refluxing with NaOH for ring closure. The following is a schematic representation of the steps to obtain the oxazepine form of reagent (Q):

A selected $R_1$ substituent in compounds of the invention is introduced by employing a commercially available reagent E amino acid or derivative thereof with a side chain that corresponds to the selected $R_1$. In the case where the desired reagent E is not commercially available, it may be synthesized from another amino acid that is commercially available using established synthetic techniques.

The $R_2$ substituent is incorporated in compounds of the invention by employing a commercially available reagent C that is derivatized at $R_2$ with the desired substituent. Reagent C wherein $R_2$ is OH, is commercially available and can serve as a starting material for synthesizing a corresponding

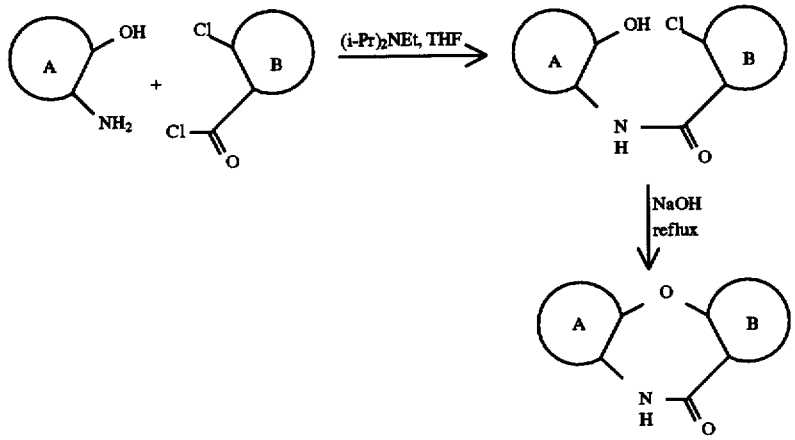

The thiepine form of reagent (Q), i.e. when $X_1$ is S and $X_2$— is CH=, may be prepared according to the procedures described by Sindelar et al (Collect. Czech. Chem. Commun, 1983, 48(4):1187). When reagent (Q) is an oxepine i.e. when $X_1$ is O and $X_2$— is $CH_2$—, it may be prepared in the manner reported by Harris et al (J. Med. Chem., 1982, 25(7):855); and the corresponding cycloheptene reagent (Q) i.e. when $X_1$ and $X_2$— are both $CH_2$, may be prepared as reported by De Paulis et al (J. Med. Chem. 1981, 24(9):1021). The thiazepine reagent (Q) may be prepared in a four step process starting from 1-bromo-2-nitrobenzene and methyl thiosalicylate. The steps involve coupling; reduction of the nitro group; hydrolysis of the ester group; and finally ring closure.

Reagents of Formula B are synthesized using established synthetic techniques from starting materials that are commercially available. Particularly, reagent B can be made by coupling two amino acids of the general formulae C and E:

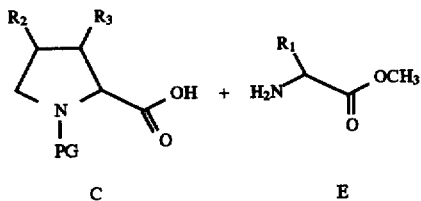

wherein $R_1$, $R_2$ and $R_3$ have the meaning described above and PG is a suitable protecting group such as Fmoc. Reagents C and E are coupled using a suitable coupling agent such as 1-(3-dimethylaminopropyl)-3-ethylcarbodiimide (EDCl) followed by deprotection and cyclization, then reduction of the resulting diketopiperazine using a suitable reducing agent such as $LiAlH_4$.

reagent C wherein $R_2$ is other than OH. Alternatively, a compound of Formula I wherein $R_2$ is OH can be subsequently derivatized, for example to the corresponding $C_{1-9}$alkoxy, $C_{1-9}$alkyl or benzyloxy, using established synthetic techniques. Similarly $R_3$ may be introduced to compounds of the invention by employing an appropriately derivatized reagent C. Again, an OH group at $R_3$ of reagent E (prepared according to the procedures described by Cooper et al, J. Chem. Soc. Perkin Trans., 1993, p.1313) can serve as the starting material to yield the selected $R_3$ substituent prior or subsequent to coupling with reagent E.

Reagent E is commercially available as a proline derivative (when n=1) or a piperidine derivative (when n=2) to give the desired bicyclic nonane or decane compound, respectively. The orientation of the chiral carbon at the 6-position (H*) of the nonane and decane is introduced according to the orientation of the reagent E. For example, when reagent E is L-proline, H* in the resulting bicyclic nonane will have an S-configuration.

For laboratory use as a ligand, the present compounds can be stored in packaged form for reconstitution and use. The present compounds can be used to distinguish dopamine receptors from other receptor types, for example glutamate and opioid receptors, within a population of receptors and in particular to distinguish between the D4 and D2 receptors. The latter can be achieved by incubating preparations of the D4 receptor and of the D2 receptor with a D4 selective compound of the invention and then incubating the resulting preparation with a radiolabelled dopamine receptor ligand, such as $^3$H-spiperone. The D2 and D4 receptors are then distinguished by determining the difference in membrane-bound radioactivity, with the D4 receptor exhibiting lesser radioactivity, i.e., lesser $^3$H-spiperone binding.

In another embodiment of the invention, the compound is provided in labelled form, such as radiolabelled form e.g.

labelled by incorporation within its structure of $^3$H or $^{14}$C or by conjugation to $^{125}$I or $^{123}$I. Such radiolabelled forms can be used directly to distinguish between dopamine D4 and dopamine D2 receptors. Furthermore, radiolabelled forms of the present compounds can be exploited to screen for more potent dopamine D4 ligands, by determining the ability of the test ligand to displace the radiolabelled compound of the present invention.

The clozapine-like binding profile of the present compounds indicate their utility as pharmaceuticals that may be useful as a neuroleptic for the treatment of various conditions in which D4 receptor stimulation is implicated, such as for the treatment of anxiety and schizophrenia.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or hydrate thereof, in an amount effective to antagonize D4 receptor stimulation.

The compounds of the present invention may be administered by any convenient route, for example by oral, parenteral, buccal, sublingual, nasal, rectal or transdermal administration and the pharmaceutical compositions formulated accordingly.

The compounds and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as flurochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Suitable unit doses i.e. therapeutically effective amounts; can be determined during clinical trials designed appropriately for each of the conditions for which administration of a chosen compound is indicated and will of course vary depending on the desired clinical endpoint. It is anticipated that dosage sizes appropriate for administering the compounds of the examples will be roughly equivalent to, or slightly less than, those used currently for clozapine.

Accordingly, each dosage unit for oral administration may contain from 1 to about 500 mgs, and will be administered in a frequency appropriate for initial and maintenance treatments.

EXAMPLE 1(a)

(S)-1,4-diazabicyclo[4.3.0]nonane

N-Fmoc-L-proline (10.11 g; 0.030 mol), glycine methyl ester hydrochloride (3.76 g; 0.030 mol), EDCl (6.89 g; 0.036 mol) and hydroxybenzotriazole (4.86 g; 0.036 mol) were dissolved in anhydrous methylene chloride (150 mL) under an atmosphere of argon. Triethylamine (8.35 mL; 0.060 mol; Aldrich) was added to this solution via syringe and the mixture was stirred overnight. The reaction mixture was then washed with water. (2×100 mL) and brine (1×100 mL), dried over MgSO$_4$ and evaporated to dryness to give a white foam (9.90 g, 81%).

The above dipeptide (9.90 g; 0.024 mol) was dissolved in methanol (100 mL) under an atmosphere of argon and triethylamine (16.84 mL; 0.12 mol) was added via syringe. The resulting mixture was heated to reflux for 2 hours, then concentrated and the diketopiperazine product precipitated by trituration with ether. A white solid was obtained (3.28 g, 88%); mp 201°–203° C.

The diketopiperazine (4.00 g; 0.026 mol) was added, portionwise, to a slurry of lithium aluminum hydride (4.03 g; 0.11 mol) in anhydrous tetrahydrofuran (100 mL). The reaction mixture was then heated to reflux for 15 minutes. Quenching was performed at 0° C. using 6 mL of water, 6 mL of 15% NaOH and finally 15 mL of water. After stirring at room temperature for 1 hour, the mixture was filtered and the filtrate concentrated to give a yellow oil which was purified by microdistillation (bp 50°–60° C.; 100 millitorr) to a colorless oil (1.98 g; 61%).

In a like manner, the following additional compounds were prepared:

b) (6R)-1,4-diazabicyclo[4.3.0]nonane; 50.3% yield; bp 50°–60° C., 100 millitorr, from N-Fmoc-D-proline;

c) (6S)-1,4-diazabicyclo[4.4.0]decane; 26% yield; bp 90°–100° C., 200 millitorr, from N-Fmoc-L-pipecolic acid;

d) (6R)-1,4-diazabicyclo[4.4.0]decane; 43% yield; bp 90°–100° C., 200 millitorr, from N-Fmoc-D-pipecolic acid;

e) (6S,8S)-8-benzyloxy-1,4-diazabicyclo[4.3.0]nonane, 77% yield, from (4S)-4-benzyloxy-L-proline and with TFA deprotection prior to cyclization;

f) (6R,S)-1,4-diazabicyclo[4.4.0]decane, 50.7% yield, bp 55° C., 100 millitorr, from N-Fmoc-D,L-pipecolic acid;

g) (6S,8S)-8-t-butoxy-1,4-diazabicyclo[4.3.0]nonane, 72% yield, from (4S)-N-Fmoc-4-t-butoxy-L-proline; and h) (3S,6S)-3-methyl-1,4-diazabicyclo[4.3.0]nonane, 14% yield, from N-Fmoc-L-proline and L-alanine methyl ester hydrochloride.

EXAMPLE 2(a)

8-chloro-11-[(S)-1,4-diazabicyclo[4.3.0]non-4-yl]-dibenzo[b,f]-1,4-oxazepine

To a stirred solution of 8-chloro-10,11-dihydrodibenz[b,f]-1,4-oxazepine-11-one (1.04 g; 4.23 mmol) in anhydrous toluene (20 mL) was added $PCl_5$ (1.06 g; 5.08 mmol) as a solid in one portion under an atmosphere of argon. The reaction mixture was heated to reflux for 4 hours, then cooled to room temperature and concentrated. The oily residue was redissolved in toluene (10 mL) and concentrated once again. Drying on a vacuum line provided the desired iminochloride as a yellow solid that was used for the next reaction without further purification.

The iminochloride (0.585 g; 2.22 mmol) was dissolved in anhydrous acetonitrile (20 mL) and DIEA (1.54 mL; 8.87 mmol) was added via syringe followed by (S)-1,4-diazabicyclo[4.3.0]nonane (0.419 g; 3.32 mmol) under an atmosphere of argon. The solution was heated to reflux overnight. After cooling to room temperature, the reaction mixture was concentrated then the residue was redissolved in methylene chloride. The solution was then washed with water (1×50 mL), dried ($MgSO_4$) and concentrated to give a yellow oil. Purification of the product was conducted on silica gel using 30% acetone in hexane as the eluent to give 0.149 (19%) mg of an off-white solid; mp 118°–120° C.; Rf(20% acetone/hexanes): 0.13; HRMS (FAB): MH$^+$ of $C_{20}H_{20}N_3OCl$, calculated 354.1373, found 354.1333; $[\alpha]_D$+ 6.73.

The hydrochloride salt of the title compound is subsequently prepared by dissolving the base (0.17 g; 0.478 mmol) in 0.5 mL of 3N-HCl in ethyl acetate, then stirring at room temperature for 15 minutes. The solution is removed under vacuum and the resulting oil was triturated with dry methanol (5 mL). The solvent is evaporated under reduced pressure to yield the hydrochloride salt; 0.177 g, 95%; mp 150° C. (dec).

In a like manner, the following additional compounds were prepared:

b) 8-chloro-11-[(R)-1,4-diazabicyclo[4.3.0]non-4-yl]-dibenzo[b,f]-1,4-oxazepine; 20% yield; mp 121°–123° C.; Rf(20% acetone/hexanes): 0.13; $[\alpha]_D$–3.09; from the bicyclic moiety of Example 1(b);

c) 8-chloro-11-[(S)-1,4-diazabicyclo[4.4.0]decan-4-yl]-dibenzo[b,f]-1,4-oxazepine; 72% yield; mp 62°–64° C.; Rf(20% acetone/hexanes): 0.27; $[\alpha]_D$–16.3; from the bicyclic moiety of Example 1(c);

d) 8-chloro-11-[(R)-1,4-diazabicyclo[4.4.0]decan-4-yl]-dibenzo[b,f]-1,4-oxazepine; 56% yield; mp 62°–64° C.; Rf(20% acetone/hexanes): 0.27; $[\alpha]_D$+15.3; from the bicyclic moiety of Example 1(d);

e) 8-chloro-11-[(6S,8S)-8-benzyloxy-1,4-diazabicyclo[4.3.0]non-4-yl]-dibenzo[b,f]-1,4-oxazepine; 24% yield; mp 56°–58° C.; Rf(20% acetone/hexanes): 0.20; HRMS (FAB) MH$^+$ of $C_{27}H_{26}N_3O_2Cl$, calculated. 460.1792, found 460.1787; from the bicyclic moiety of Example 1(e);

f) 8-chloro-11-[(R,S)-1,4-diazabicyclo[4.4.0]decan-4-yl]-dibenzo[b,f]-1,4-oxazepine; 16% yield; mp 61°–64° C., from the bicyclic moiety of Example 1(f); and g) 8-chloro-11-[(6S,8S)-8-t-butoxy-1,4-diazabicyclo[4.4.0]decan-4-yl]-dibenzo[b,f]-1,4-oxazepine; mp 119°–121° C.; Rf(25% acetone/hexanes): 0.26; HRMS (FAB): MH$^+$ of $C_{24}H_{28}N_3O_2Cl$, calculated 426.1984, found 426.1964; from the bicyclic moiety of Example 1(g).

EXAMPLE 3

8-chloro-11-[(6S,8S)-8-hydroxy-1,4-diazabicyclo[4.3.0]non-4-yl]-dibenzo[b,f]-1,4-oxazepine 8-chloro-11-[(6S,8S)-8-t-butoxy-1,4-diazabicyclo[4.3.0]non-4-yl]-dibenzo[b,f]-1,4-oxazepine (0.211 g, 0.495 mmol), prepared as described above, was dissolved in trifluoroacetic acid (10 mL) and stirred for 15 minutes. The solvent was removed and the resulting residue was redissolved in methylene chloride (20 mL). Triethylamine (0.100 g, 0.991 mmol) was then added via syringe and the resulting solution was stirred for 1 hour. Washing with water (50 mL), drying over $MgSO_4$ and concentrating resulted in a white solid (0.180 g, 99%); mp 94°–96° C.; Rf(35% acetone/hexanes): 0:15; HRMS (FAB) MH$^+$ of $C_{20}H_{20}N_3O_2Cl$, calculated 370.1322, found 370.1318.

EXAMPLE 4(a)

8-chloro-11-[(6S,8S)-8-methoxy-1,4-diazabicyclo[4.3.0]non-4-yl]-dibenzo[b,f]-1,4-oxazepine To a suspension of NaH (5 mg, 0.203 mmol) in anhydrous N,N-dimethylformamide (5 mL) at 0° C. was added 8-chloro-11-[(6S,8S)-8-hydroxy-1,4-diazabicyclo[4.3.0]non-4-yl]-dibenzo[b,f]-1,4-oxazepine (50 mg, 0.135 mmol) as a solution in anhydrous N,N-dimethylformamide (5 mL) under argon. The mixture was stirred at 0° C. for 15 minutes then at room temperature for 30 minutes, then cooled back to 0° C. and methyl iodide (28.6 mg, 0.201 mmol) was added via syringe. The solution was allowed to warm to room temperature and was stirred overnight, quenched with water (0.5 mL) and the product extracted into ether. The combined organic layers were washed with brine, dried ($MgSO_4$) and evaporated to dryness. The product was purified on silica gel using 30% acetone in hexanes as the eluent to give 12 mg (23%) of an off-white solid; mp 70°–72° C.; Rf (30% acetone/hexanes): 0.20; HRMS (FAB): MH$^+$ of $C_{21}H_{22}N_3O_2Cl$, calculated 384.1479, found 384.1468.

In a like manner, the following additional compound was prepared:

(b) 8-chloro-11-[(6S,8S)-8-piperonyloxy-1,4-diazabicyclo[4.3.0]non-4-yl]-dibenzo[b,f]-1,4-oxazepine; Rf(30% acetone/hexanes): 0.50; HRMS (FAB): MH$^+$ of $C_{28}H_{26}N_3O_4Cl$, calculated 504.1690, found 504.1662.

EXAMPLE 5

8-chloro-11-[(6S,8R)-8-hydroxy-1,4-diazabicyclo[4.3.0]non-4-yl]-dibenz[b,f]-1,4-oxazepine To a solution of 8-chloro-11-[(6S,8S)-8-hydroxy-1,4-diazabicyclo[4.3.0]non-4-yl]-dibenz[b,f]-1,4-oxazepine (64 mg, 0.173 mmol), benzoic acid (42.3 mg, 0.346 mmol) and triphenylphosphine (91.0 mg, 0.346 mmol) in anhydrous methylene chloride (20 mL) at 0° C. under argon was added diethyl azodicarboxylate (60.3 mg, 0.346 mmol) via syringe. The reaction mixture was allowed to warm to room temperature and was stirred overnight. The product was absorbed onto silica gel and purified by flash column chromatography using 10% acetone in hexanes as the eluent to give 51.6 mg (63%) of 8-chloro-11-[(6S,8R)-8-benzoyl-1,4-diazabicyclo[4.3.0]non-4-yl]-dibenz[b,f]-1,4-oxazepine as an off-white solid; mp (succinic acid salt) 92°–94° C.; Rf(25% acetone/hexanes): 0.45; HRMS (FAB): MH$^+$ of $C_{27}H_{24}N_3O_3Cl$, calculated 474.1584, found 474.1595.

To a solution of 8-chloro-11-[(6S,8R)-8-benzoyl-1,4-diazabicyclo[4.3.0]non-4-yl]-dibenz[b,f]-1,4-oxazepine in methanol (5 mL) was added 1% aqueous sodium hydroxide. The reaction was stirred for 1 hour and the solvent removed under reduced pressure. The residue was dissolved in methylene chloride and washed with water, dried (MgSO$_4$) and evaporated to dryness to give 3.5 mg (31%) of 8-chloro-11-[(6S,8R)-8-hydroxy-1,4-diazabicyclo[4.3.0]non-4-yl]-dibenz[b,f]-1,4-oxazepine as an off-white solid; mp 90°–92° C.; Rf(50% acetone/hexanes): 0.20; HRMS (FAB): MH$^+$ of $C_{20}H_{20}N_3O_2Cl$, calculated 370.1322, found 370.1327.

EXAMPLE 6(a)

4-chloro-11-[(6S)-1,4-diazabicyclo[4.3.0]non-4-yl]-dibenzo[b,f]-1,4-oxazepine

2-Aminophenol (20.7 g, 0.19 mol), 2,3-dichlorbenzoic acid (36.3 g, 0.19 mol) and dimethylaminopyridine (2.32 g, 0.019 mol) were dissolved in methylene chloride (410 mL) in a 1 L Erlenmeyer flask and cooled to 5° C. before 1-(3-dimethylaminopropyl)-3-ethylcarbodiimide (40 g, 0.209 mol) was added as a solid. The reaction mixture was allowed to stir overnight at room temperature. The resulting red solution was concentrated to give a viscous red/brown liquid to which water was added and the product allowed to solidify for two days with occasional stirring. The product was collected by suction filtration, washed several times with water and minimal amounts of cold ethanol to give 42.5 g (79%) of yellow crystals of N-(2-hydroxyphenyl)-2,3-dichlorobenzamide which was used for the next reaction without further purification.

To a solution of N-(2-hydroxyphenyl)-2,3-dichlorobenzamide (29 g, 0.103 mol) in N,N-dimethylformamide (250 mL) was added potassium hydroxide flakes (5.9 g, 0.105 mol). The reaction mixture was refluxed for 24 hours, then cooled to room temperature and poured into ice water (1.3 L) to produce a tan coloured solid. The precipitate was collected by suction filtration, washed several times with water and then 5% aqueous potassium hydroxide solution until the filtrate was colourless and finally washed with water and air dried to give 23 g (92%) of a grey solid which was recystallized from acetone to give fine off-white needles.

The iminochloride of 4-chloro-10,11-dihydrodibenz[b,f]-1,4-oxazepine-11-one was next prepared in a like manner to the iminochloride of 8-chloro-10,11-dihydrodibenz[b,f]-1,4-oxazepine-11-one described in Example 2(a). The iminochloride (1.82 g, 6.89 mmol) was then dissolved in anhydrous acetonitrile (50 mL) under argon and diisopropylethylamine (3.36 g, 26 mmol) was added via syringe followed by (S)-1,4-diazabicyclo[4.3.0]nonane (1.23 g, 9.75 mmol). The solution was heated to reflux for 5 hours. After cooling to room temperature, the reaction mixture was concentrated and the residue redissolved in methylene chloride, washed with water and brine. The combined aqueous layers were re-extracted with methylene chloride, then the combined organic layers were dried (MgSO$_4$) and the crude product absorbed onto silica gel and purified by flash column chromatography using 20% acetone in hexanes as the eluent to give 0.970 g (40%) of a yellow solid which was recrystallized from hexanes to give light yellow crystals; mp 146°–148° C.; Rf (20% acetone/hexanes): 0.10; HRMS (FAB): MH$^+$ of $C_{20}H_{20}N_3OCl$, calculated 354.1373, found 354.1365.

In a like manner, the following additional compound is prepared:

b) 4-chloro-11-[(6R)-1,4-diazabicyclo[4.3.0]non-4-yl]-dibenzo[b,f]-1,4-oxazepine, 49% yield, m.p. 150°–151° C., Rf (20% acetone/hexanes): 0.15, from the bicyclic moiety of Example 1(b).

Also in a like manner, compounds of Formula I are generated by coupling the bicyclic moieties of Example 1 to other tricyclic moieties, including:

c) 4-nitro-10,11-dihydrodibenz[b,f]-1,4-oxazepine-11-one
d) 4-amino-10,11-dihydrodibenz[b,f]-1,4-oxazepine-11-one, obtained as follows:

The 4-nitro compound of Example 4(c) (2.56 g, 10.0 mmol) was reduced by zinc dust (19.6 g, 300 mmol) in the presence of calcium chloride dihydrate (1.03 g, 7.00 mmol) in EtOH (78%) (100 mL) to afford 2.04 g (90%) of the title compound, m.p. 230° C.

e) 4-bromo-10,11-dihydrodibenz[b,f]-1,4-oxazepine-11-one prepared as follows:

To the mixture of copper(II) bromide (1.12 g, 5.00 mmol) and tert-butyl nitrite (0.71 g, 6.88 mmol) in acetonitrile (20.0 mL) was added the solution of 4-amino-10,11-dihydrodibenz[b,f]-1,4-oxazepine-11-one of Example 4(d) (0.91 g, 4.00 mmol) in acetonitrile (10.0 mL) and N,N-dimethylformamide (10.0 mL) at 50° C. (oil bath). The resulting mixture was kept at 50° C. for 30 min before it was cooled to room temperature and poured onto 200 mL of 1N hydrochloric acid. The aqueous solution was extracted with ethyl acetate (3×). The combined ethyl acetate solution was dried (MgSO$_4$) and filtered. The filtrate was concentrated in vacuo to dryness. The crude material was chromatographed (33% EtOAc/Hexane); yield 0.96 g (83%); m.p. 220°–222° C.; MS (FAB) 290, 292 (M$^+$+1).

EXAMPLE 7(a)

8-chloro-11-[(6S,8S)-8-hydroxy-1,4-diazabicyclo[4.3.0]non-4-yl]-dibenz[b,f]-1,4-thiazepine A solution of NaH (1.1 g, 0.04 mol) in dry THF (20 mL) was cooled to 0° C. To this mixture methyl thiosalicylate (5.1 mL, 0.036 mol) was added dropwise via syringe. The reaction mixture was warmed to room temperature to ensure completion of the reaction. The solution was cooled to 0° C. and 2,5-dichloronitrobenzene (7.0 g, 0.036 mol) was added dropwise in THF (20 mL). The reaction was stirred at 0° C. for 30 min then stirred at room temperature for 4 hrs. The reaction was quenched with 5 mL ice cold water and then diluted with EtOAc (300 mL). The phases were separated and the organic phase was washed with sat. NaHCO$_3$, water and brine. The organic phase was dried (MgSO$_4$) and concentrated in vacuo. Recrystallization was done in CHCl$_3$ and Et$_2$O; to yield 2-nitro-4-chloro-2'-methoxycarbonyl-diphenylsulfide 10.9 g, (93%).

To a solution of 2-nitro-4-chloro-2'-methoxycarbonyl-diphenylsulfide (10.3 g, 0.032 mol) in 78% ethanol (200 mL) a solution of CaCl$_2$ (2.3 g, 0.019 mol) in 4 mL water was added. Zn dust (68.9 g, 1.05 mol) was added and the mixture was refluxed for 3 hrs. The hot mixture was filtered through a celite pad and washed with hot ethanol. The filtrate was concentrated in vacuo to obtain the solid 2-amino-4-chloro-2'-methoxycarbonyl-diphenylsulfide; yield 10.01 g, (98%).

To a solution of 2-amino-4-chloro-2'-methoxycarbonyl-diphenylsulfide (9.4 g, 0.032 mol) in ethanol, was added 1N KOH (67 mL, 0.067 mol) and the mixture refluxed for 2 hrs. The ethanol was removed and the solution was cooled to 0° C. The product 2-amino-4-chloro-2'-carboxyl-diphenylsulfide was precipitated by dropwise addition of conc. HCl to pH3. The precipitate was filtered and collected and dried; yield 8.5 g, (95%).

To a solution of 2-amino-4-chloro-2'-carboxyl-diphenylsulfide (8.4 g, 0.03 mol) in dry CH$_2$Cl$_2$, was added 4-dimethylaminopyridine (1.2 g, 0.009 mol) and 1-(3-dimethylaminopropyl)-3-ethylcarbodiimide hydrochloride (10.1 g, 0.053 mol) and stirred at room temperature overnight. The solution was concentrated in vacuo, then diluted with water (200 mL) and ether (50 mL) and placed in refrigerator. The precipitate 8-chloro-10,11-dihydrodibenz[b,f]-1,4-thiazepine-11-one was filtered and dried under vacuum; yield 7.2 g, (92%).

The iminochloride of 8-chloro-10,11-dihydrodibenz[b,f]-1,4-thiazepine-11-one (0.580 g, 2.07 mmol), prepared in a like manner to the iminochloride of 8-chloro-10,11-dihydrodibenz[b,f]-1,4-oxazepine-11-one described in example 2(a), was dissolved in anhydrous acetonitrile (20 mL) under argon and (6S,8S)-8-t-butoxy-1,4-diazabicyclo[4.3.0]nonane (0.970 g, 4.89 mmol) was added as a solution in anhydrous acetonitrile (5 mL) via syringe and the resulting solution was heated to reflux for 5 hours. After cooling to room temperature, the solvent was evaporated under reduced pressure and the residue partitioned between water and methylene chloride. The organic layer was washed with brine, dried (MgSO$_4$) and evaporated to dryness. The product was purified on silica gel using 10% acetone in hexanes as the eluent to give 0.34 g (37%) of 8-chloro-11-[(6S,8S)-8-t-butoxy-1,4-diazabicyclo[4.3.0]non-4-yl]-dibenz[b,f]-1,4-thiazepine as an off-white solid; mp 132°–134° C.; Rf (10% acetone/hexanes): 0.10; HRMS (FAB): MH$^+$ of C$_{24}$H$_{28}$N$_3$OSCl, calculated 442.1720, found 442.1728.

8-chloro-11-[(6S,8S)-8-t-butoxy-1,4-diazabicyclo[4.3.0]non-4-yl]-dibenz[b,f]-1,4-thiazepine (0.311 g, 0.704 mmol) was dissolved in trifluoroacetic acid (20 mL) and stirred for 1 hour. The trifluoroacetic acid was removed under reduced pressure and the residue dissolved in methylene chloride (20 mL). Triethylamine (0.142 g, 1.40 mmol) was then added via syringe and the reaction stirred for 1 hour, washed with water, dried (MgSO$_4$) and evaporated to dryness to give 8-chloro-11-[(6S,8S)-8-hydroxy-1,4-diazabicyclo[4.3.0]non-4-yl]-dibenz[b,f]-1,4-thiazepine as an off-white solid (0.197 g, 72%); mp 58°–60° C.; Rf (40% acetone/hexanes): 0.15; HRMS (FAB): MH$^+$ of C$_{20}$H$_{20}$N$_3$OSCl, calculated 386.1094, found 386.1085.

b) In the manner described, the 10,11-dihydrodibenz[b,f]-1,4-thiazepine-11-one is prepared starting from 1-bromo-2-nitrobenzene, and compounds of Formula I are prepared by coupling the bicyclic moieties of Example 1 to generate the corresponding unsubstituted dibenz[b,f]-1,4-thiazepines.

EXAMPLE 8

Receptor Binding Assay

D2 and D4 receptor-binding affinities of compounds of the Examples were evaluated according to their ability to reduce binding of $^3$H-spiperone as compared to the reference compound clozapine. The potency of the test compound to reduce $^3$H-spiperone binding directly correlated to its binding affinity for the receptor.

D4 Receptor Preparation

HEK 298 (human embryonic kidney) cells stably transfected with human D4 receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 min, 5000 rpm (GS3 rotor) and the pellets quickly frozen in liquid nitrogen and stored at –80° C. until used in binding assay. When used in the assay, cells were thawed on ice for 20 min and then 1 mL of incubation buffer (50 mM Tris, 1 mM EDTA, 4 mM MgCl$_2$, 5 mM KCl, 1.5 mM CaCl$_2$, 120 mM NaCl, pH$_{7.4}$) was added. The cells were then vortexed to resuspend pellet and homogenized with a Kinematica CH-6010 Kriens-LU homogenizer for 15 seconds at setting 7. Concentration of receptor protein was determined using the Pierce BCA assay.

D2 Receptor Preparation

GH$_4$C$_1$ (rat pituitary) cells stably transfected with the human D2 receptor (short isoform) were grown in CO$_2$ independent media in roller bottles (1500 cm$^2$) for 10 days. 100 µM ZnSO$_4$ was added to the cells (the D2 promoter being zinc inducible). After 16 hours, fresh media was added to allow the cells to recover for 24 hours. The cells were harvested using versine and then centrifuged in a Sorval centrifuge for 10 minutes, at 5000 rpm (GS3 rotor). Pellets were quickly frozen in liquid nitrogen and stored at –80° C. until used in the binding assays. When used in the assay, cells were thawed on ice for 20 minutes. Each roller bottle produced approximately 72 mg of protein. 10 ml of incubation buffer was added to the pellets which were then vortexed, resuspended and homogenized with a Kinematica CH-6010 Kriens-LU homogenizer for 15 seconds at setting 7. The receptor protein concentration was determined using the Pierce BCA assay.

Total Spiperone Binding Assay

The incubation was started by the addition of 500 µl (50 µg protein) membrane homogenate to a solution of 900 µl incubation buffer and 100 µl (0.25 nM final conc.) $^3$H-spiperone (90 Ci/mmol Amersham diluted in borosilicate glass vial) in 12×75 mm polypropylene tubes. The tubes were vortexed and incubated at room temperature for 90 minutes. The binding reaction was stopped by filtering using a Brandell Cell Harvester. The samples were filtered under vacuum over glass fibre filters (Whatman GF/B) presoaked for 2 hours in 0.3% polyethylenimine (PEI) in 50 mM Tris buffer (pH 7.4). The filters were then washed 3 times with 5 ml ice cold 50 mM Tris buffer (pH 7.4). Individual filter disks were put in scintillation vials (Biovials, Bechman). Ready Protein Plus liquid scintillant (5 ml, Beckman) was added and the vials counted by liquid scintillation spectrophotometry (Beckman LSC 6500) after equilibrating for three hours at room temperature to determine total binding (B$_T$).

Non-Specific Binding Assay for D4

The incubation was started by the addition of 500 µl (50 µg protein) membrane homogenate to a solution of 400 µl incubation buffer, 100 µl $^3$H-spiperone (90 Ci/mmol Amersham diluted in borosilicate glass vial to 0.25 nM final conc.) and 500 µl (30 µM final conc.) of fresh dopamine (Research Biochemicals Inc., light protected and dissolved in incubation buffer) in 12×75 mm polypropylene tubes. The tubes were vortexed and incubated at room temperature for 90 minutes at which time the binding reaction was stopped by filtering. The filters were washed and counted using the same procedure as in the total binding assay described above to give the non-specific binding value (NSB).

Non-Specific Binding Assay for D2

This assay employed the same procedures as the non-specific binding assay for D4 with the exception that 2 µM (final conc.) of (−) sulpiride (Research Chemicals Inc.) was used in place of dopamine.

Displacement Binding Assay

The incubation was started by the addition to 12×75 mm polypropylene tubes 500 µl (50 µg protein) membrane homogenate to a solution of 400 µl incubation buffer, 100 µl (0.25 final conc.) $^3$H-spiperone (90 Ci/mmol, Amersham, diluted in borosilicate glass vial to) and 500 µl of test compound that was prepared from 1 mM stock dissolved in DMSO and stored at −20° C. in polypropylene cryogenic storage vials until dilution in incubation buffer in borosilicate glass vials. The tubes were vortexed and incubated at room temperature for 90 minutes at which time the binding reaction was stopped by filtering. The filters were washed and counted using the same procedure as in the total binding assay described above to give the displacement binding value ($B_D$).

Calculations

The test compounds were initially assayed at 1 and 0.1 µM and then at a range of concentrations chosen such that the middle dose would cause about 50% inhibition of $^3$H-spiperone binding. Specific binding in the absence of test compound ($B_0$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of %B/B$_0$ vs concentration of test compound.

Ki was calculated by the Cheng and Prustoff transformation: $Ki=IC_{50}/(1+[L]/K_D)$ where [L] is the concentration of $^3$H-spiperone used in the assay and $K_D$ is the dissociation constant of $^3$H-spiperone determined independently under the same binding conditions.

Assay results are reported in the following Table, and show clearly the advantage in terms of D4 selectivity and or binding affinity of compounds of the invention over clozapine.

D4 AFFINITY AND SELECTIVITY

| COMPOUND | STRUCTURE | Ki | D2/D4 |
|---|---|---|---|
| clozapine | 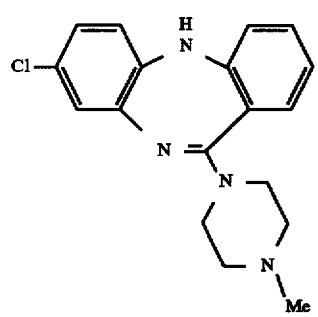 | 23 | 10 |
| 8-chloro-11-[(S)-1,4-diazabicyclo[4.3.0]non-4-yl]-dibenzo[b,f]-1,4-oxazepine | 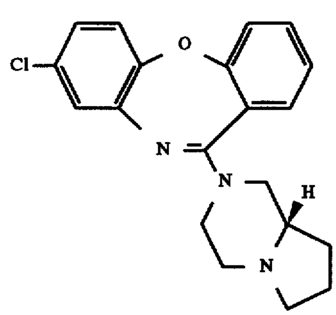 | 1.2 | 104.5 |

-continued

D4 AFFINITY AND SELECTIVITY

| COMPOUND | STRUCTURE | Ki | D2/D4 |
|---|---|---|---|
| 8-chloro-11-[(R)-1,4 diazabicyclo[4.3.0]non-4-yl]-dibenzo[b,f]-1,4-oxazepine | 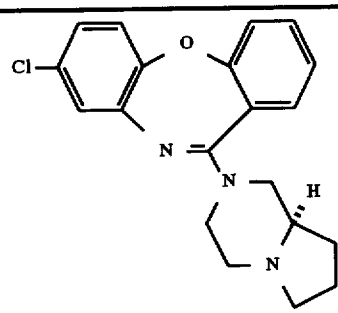 | 18 | 32.2 |
| 8-chloro-11-[(S)-1,4 diazabicyclo[4.4.0]decan-4-yl]-dibenzo[b,f]-1,4-oxazepine | 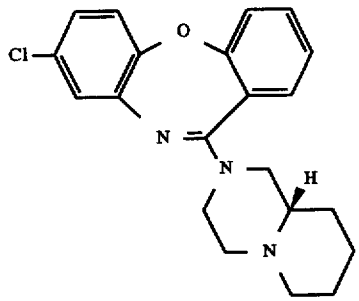 | 1 | 40 |
| 8-chloro-11-[(R)-1,4-diazabicyclo[4.4.0]decan-4-yl]-dibenzo[b,f]-1,4-oxazepine | 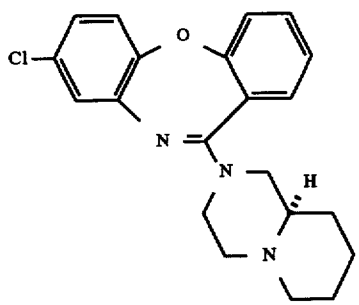 | 402 | 4.1 |
| 8-chloro-11-[(6S)-8-benzyloxy-1,4-diazabicyclo[4.3.0]non-4-yl]-dibenzo[b,f]-1,4-oxazepine | 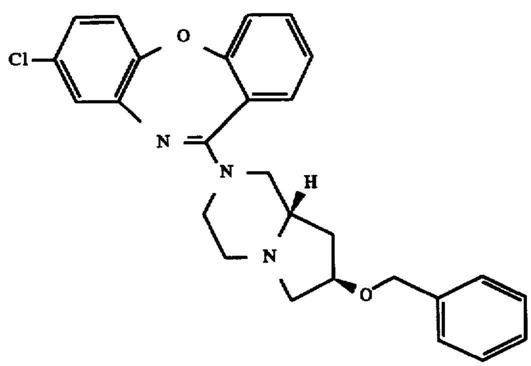 | 24 | 25.6 |
| 8-chloro-11-[(6S)-8-hydroxy-1,4-diazabicyclo[4.3.0]non-4-yl]-dibenzo[b,f]-1,4-oxazepine | 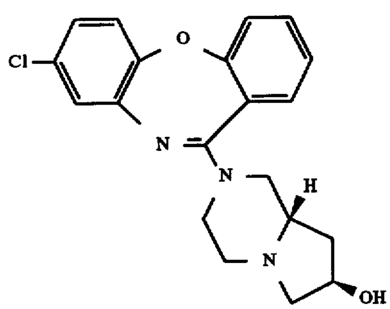 | 28 | 18.2 |

D4 AFFINITY AND SELECTIVITY

| COMPOUND | STRUCTURE | Ki | D2/D4 |
|---|---|---|---|
| 8-chloro-11-[(R,S)-1,4-diazabicyclo[4.4.0]decan-4-yl]-dibenzo[b,f]-1,4-oxazepine | 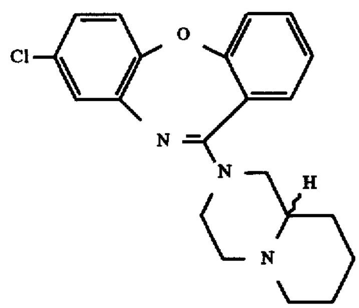 | 15.7 | 6.8 |

EXAMPLE 5

Functional Assay

The D4 receptor responds to dopamine and other agonists by reducing adenyl cyclase mediated production of cyclic AMP. Particular test compounds were assayed for their ability to reverse dopamine inhibition of adenyl cyclase by the following procedure. Forskolin was used to elevate the basal adenyl cyclase activity.

CHO Pro 5 cells stably expressing human D4 receptors were plated in 6 well plates in DMEM (Dulbecco's Modified Eagle Medium)/F12(Nutrient Mixture F12 (Ham)) media with 10% FCS (fetal calf serum) and G418 (Geneticen Disulfate), and incubated at 37° C. in a $CO_2$ incubator. The cells were allowed to grow to about 70% confluence before use in the assay.

Antagonist Assay

The culture media of each well was removed by aspiration, and the wells were washed once with serum free media (SFM) (DMEM/F12) media. Then 2 mL of fresh SFM+IBMX media (SFM with 0.5 mM IBMX (3-isobutyl-1-methylxanthine 0.1% ascorbic acid and 10 µM pargyline) was added to each well and then incubated at 37° C. for 10 minutes in $CO_2$ incubator. Following incubation, SFM+IBMX media was aspirated and fresh SFM+IBMX media was added to wells separately with one of a) forskolin (10 µM final conc.); b) dopamine and forskolin (both 10 µM final conc.); and c) test compound (1 and 0.1 µM), and dopamine and forskolin (both 10 µM final conc.). Basal adenyl cyclase activity was determined from wells with only SFM+IBMX media added.

The cells were then incubated at 37° C. for 30 minutes in a $CO_2$ incubator. Following incubation the media was aspirated from each well and then washed once with 2 mL of PBS (phosphate buffered saline). Each well was then treated with 1 mL cold 95% ethanol:5 mM EDTA (2:1) at 4° C. for 1 hr. The cells from each well were then scraped and transferred into individual Eppendorf tubes. The tubes were centrifuged for 5 min at 4° C., and the supernatants were transferred to new Eppendorf tubes. The pellets were discarded and the supernatants dried using a SpeedVac. The extracts were then reconstituted in 600 µL of 0.1M sodium acetate buffer, pH 6.1, and stored at 4° C. until assayed for cAMP concentration. cAMP content measured in fmoles/well for each extract was determined by EIA (enzyme-immunoassay) using Amersham Biotrak cAMP EIA kit (Amersham RPN 225).

Total inhibition ($I_0$) of forskolin-stimulated adenyl cyclase activity by dopamine was determined as the difference in concentration of cAMP in the forskolin-treated cells ($C_f$) and dopamine-forskolin treated cells ($C_d$).

$$I_0 = C_f - C_d$$

Net inhibition (I) of forskolin-stimulated adenyl cyclase activity by dopamine in the presence of an antagonist was determined as the difference in concentration of cAMP in the forskolin-treated cells ($C_f$) and test compound, dopamine and forskolin treated cells (C).

$$I = C_f - C$$

The ability of the test compounds to reverse the dopamine inhibition (% reversal, %R) was determined by the formula:

$$\%R = (1 - I/I_0) \times 100$$

| COMPOUND | % REVERSAL OF DOPAMINE EFFECT | |
|---|---|---|
| | 1 µM | 10 µM |
| clozapine | 10 | 62 |
| 8-chloro-11-[(S)-1,4-diazabicyclo[4.3.0]-non-4-yl]dibenzo[b,f]-1,4-oxazepine | 23 | 48 |
| 8-chloro-11-[(S)-1,4-diazabicyclo[4.4.0]-decan-4-yl]-dibenzo[b,f]-1,4-oxazepine | 52 | 93 |

Agonist Assay

To D4 stably expressing CHO cells prepared as previously described were added test compound and forskolin (10 µM final concentration). The cells were incubated, extracted and measured for cAMP concentration as above. Agonist activity of a test compound would result in a decrease in cAMP concentration compared to cells treated with forskolin ($C_f$) only. No decrease was observed, therefore the test compounds exhibited no dopamine agonist activity. It is predicted based on structural and biological functional similarities that the remaining compounds of the invention would also exhibit dopamine antagonist activity.

We claim:
1. A compound of Formula I:

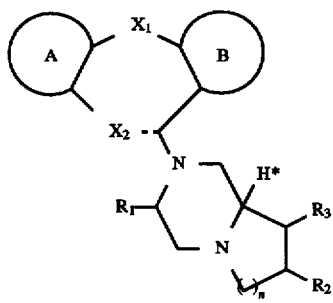

wherein:
A and B are independently selected from substituted or unsubstituted benzene;
$X_1$ is selected from O, S, SO, and $SO_2$;
$X_2$— is N=;
n is 1 or 2;
$R_1$ is selected from H and the α-carbon side chain of an amino acid;
$R_2$ and $R_3$ are selected independently from H, OH, —$NH_2$, —C(O)$NH_2$, =O, =S, halo, cyano, $C_{1-9}$alkyl, $C_{1-9}$alkoxy, $C_{1-4}$alkylS—, $C_{1-4}$alkylSO—, $C_{1-4}$alkyl$SO_2$—, phenoxy, benzyloxy and piperonyloxy; and
H* is in either the R- or the S-configuration, and acid addition salts, solvates and hydrates thereof.

2. The compound according to claim 1, wherein H* is in the S-configuration.
3. The compound according to claim 1, wherein $R_2$ is selected from H, OH and benzyloxy.
4. The compound according to claim 1, wherein $R_3$ is H.
5. The compound according to claim 1, wherein $R_1$ is H.
6. The compound according to claim 1, wherein n is 1.
7. The compound according to claim 1, wherein $R_2$ is selected from H and benzyloxy.
8. A compound according to claim 1, wherein $R_3$ and $R_1$ are H.
9. A compound according to claim 8, wherein H* is in the S-configuration.
10. A compound according to claim 9, wherein n is 1.
11. A compound according to claim 10, wherein $R_2$ is selected from H, OH and benzyloxy.
12. A compound according to claim 1, wherein H*, $R_1$, $R_2$, $R_3$ and n are selected to form the group (6S)-1,4-diazabicyclo[4.3.0]non4-yl.
13. The compound according to claim 1, wherein $X_1$ is O or S.
14. The compound according to claim 1, wherein $X_2$ is N=.
15. The compound according to claim 1, wherein A and B are independently selected from benzene and benzene substituted with 1 or 2 substituents selected independently from hydroxyl, halo, $C_{1-4}$alkyl, amino, nitro, cyano, halo-substituted $C_{1-4}$alkyl, $C_{1-4}$alkoxy, halo-substituted $C_{1-4}$alkoxy, $C_{1-4}$alkoxycarbonyl, $C_{1-4}$acyl, cyclo-$C_{1-7}$alkyl, thio-$C_{1-4}$alkylene, $C_{1-4}$alkylthio, halo-substituted $C_{1-4}$alkylthio, cyanothio, tetrazolyl, N-piperidinyl, N-piperazinyl, N-morpholinyl, acetamido, $C_{1-4}$alkylsulfonyl, halosulfonyl, halo-substituted $C_{1-4}$alkylsulfonyl, $C_{1-4}$alkylsulfoxyl, sulfonamido, $C_{1-4}$alkylseleno, and $OSO_3H$.

16. The compound according to claim 15, wherein said substituents are selected from fluoro, chloro, bromo, nitro, amino and cyano.
17. The compound according to claim 1, wherein A, B, $X_1$ and $X_2$ together are selected to form a tricycle which is an optionally substituted dibenz[b,f]-1,4-oxazepine.
18. The compound according to claim 17, wherein said tricycle is a 4-chlorodibenz[b,f]-1,4-oxazepine.
19. The compound according to claim 18, wherein $R_3$ and $R_1$ are H.
20. The compound according to claim 19, wherein H* is in the S-configuration.
21. The compound according to claim 20, wherein n is 1.
22. The compound according to claim 21, wherein $R_2$ is selected from H, OH and benzyloxy.
23. A compound according to claim 17, wherein said tricycle is a 8-chlorodibenz[b,f]-1,4-oxazepine.
24. The compound according to claim 1, wherein said compound is selected from the group consisting of:

8-chloro-11-[(6R,S)-1,4-diazabicyclo[4.4.0]decan-4-yl]dibenzo[b,f]-1,4-oxazepine;
4-chloro-11-[(6S)-1,4-diazabicyclo[4.3.0]non-4-yl]dibenzo[b,f]-1,4-oxazepine;
8-chloro-11-[(6R)-1,4-diazabicyclo[4.3.0]non-4-yl]dibenzo[b,f]-1,4-oxazepine; and
8-chloro-11-[(6R)-1,4-diazabicyclo[4.4.0]decan-4-yl]dibenzo[b,f]-1,4-oxazepine.

25. The compound according to claim 24, wherein said compound is 4-chloro-11-[(6S)-1,4-diazabicyclo[4.3.0]non-4-yl]dibenzo[b,f]-1,4-oxazepine.
26. A pharmaceutical composition, comprising a compound according to claim 1 in an amount effective to antagonize D4 receptor stimulation, and a pharmaceutically acceptable carrier.
27. A pharmaceutical composition, comprising a compound according to claim 2 in an amount effective to antagonize D4 receptor stimulation, and a pharmaceutically acceptable carrier.
28. A pharmaceutical composition, comprising a compound according to claim 12 in an amount effective to antagonize D4 receptor stimulation, and a pharmaceutically acceptable carrier.
29. A pharmaceutical composition, comprising a compound according to claim 25 in an amount effective to antagonize D4 receptor stimulation, and a pharmaceutically acceptable carrier.
30. A pharmaceutical composition, comprising a compound according to claim 1 wherein said compound is present in an amount sufficient to produce an antischizophrenia effect, and a pharmaceutically acceptable carrier.
31. A pharmaceutical composition, comprising a compound according to claim 2 wherein said compound is present in an amount sufficient to produce an antischizophrenia effect, and a pharmaceutically acceptable carrier.
32. A pharmaceutical composition, comprising a compound according to claim 12 wherein said compound is present in an amount sufficient to produce an antischizophrenia effect, and a pharmaceutically acceptable carrier.
33. A pharmaceutical composition, comprising a compound according to claim 25 wherein said compound is present in an amount sufficient to produce an antischizophrenia effect, and a pharmaceutically acceptable carrier.
34. A pharmaceutical composition comprising a compound according to claim 1, wherein said compound is present in an amount sufficient to produce an anti-anxiety effect, and a pharmaceutically acceptable carrier.

35. A method for the treatment of a medical condition mediated by D4 receptor stimulation, comprising administering to a mammal in need of such treatment, a composition according to claim 26.

36. A method for the treatment of a medical condition mediated by D4 receptor stimulation, comprising administering to a mammal in need of such treatment, a composition according to claim 27.

37. A method for the treatment of a medical condition mediated by D4 receptor stimulation, comprising administering to a mammal in need of such treatment, a composition according to claim 28.

38. A method for the treatment of a medical condition mediated by D4 receptor stimulation, comprising administering to a mammal in need of such treatment, a composition according to claim 29.

39. A method for the treatment of schizophrenia, comprising administering to a mammal in need of such treatment, a composition according to claim 30.

40. A method for the treatment of schizophrenia, comprising administering to a mammal in need of such treatment, a composition according to claim 31.

41. A method for the treatment of schizophrenia, comprising administering to a mammal in need of such treatment, a composition according to claim 32.

42. A method for the treatment of schizophrenia, comprising administering to a mammal in need of such treatment, a composition according to claim 33.

43. A method for the treatment of anxiety, comprising administering to a mammal in need of such treatment, a composition according to claim 34.

* * * * *